US011666529B2

(12) United States Patent
Sullivan et al.

(10) Patent No.: US 11,666,529 B2
(45) Date of Patent: Jun. 6, 2023

(54) USE OF PRG4 TO IMPROVE DYNAMIC VISUAL ACUITY AND HIGHER ORDER ABERRATIONS (71) Applicant: Lubris LLC, Framingham, MA (US)

(72) Inventors: Benjamin D. Sullivan, San Diego, CA (US); Edward R. Truitt, III, Medina, WA (US)

(73) Assignee: Lubris LLC, Naples, FL (US)

( * ) Notice: Subject to any disclaimer, the term of this patent is extended or adjusted under 35 U.S.C. 154(b) by 569 days.

(21) Appl. No.: 15/574,712

(22) PCT Filed: May 19, 2016

(86) PCT No.: PCT/US2016/033248
§ 371 (c)(1),
(2) Date: Nov. 16, 2017

(87) PCT Pub. No.: WO2016/187414
PCT Pub. Date: Nov. 24, 2016

(65) Prior Publication Data
US 2018/0140546 A1 May 24, 2018

Related U.S. Application Data (60) Provisional application No. 62/163,753, filed on May 19, 2015.

(51) Int. Cl.
| *A61K 8/42* | (2006.01) |
| *A61K 31/164* | (2006.01) |
| *A61K 31/165* | (2006.01) |
| *A61K 31/404* | (2006.01) |
| *A61K 31/4164* | (2006.01) |
| *A61K 9/70* | (2006.01) |
| *A61K 8/49* | (2006.01) |
| *A61K 9/06* | (2006.01) |
| *A61Q 19/00* | (2006.01) |
| *A61K 8/02* | (2006.01) |
| *A61P 17/00* | (2006.01) |
| *A61K 8/44* | (2006.01) |
| *A61Q 19/08* | (2006.01) |
| *A61K 9/00* | (2006.01) |
| *A61K 45/06* | (2006.01) |
| *A61P 27/02* | (2006.01) |
| *A61K 38/17* | (2006.01) |

(52) U.S. Cl.
CPC ........ *A61K 9/0048* (2013.01); *A61K 38/1709* (2013.01); *A61K 45/06* (2013.01); *A61P 27/02* (2018.01)

(58) Field of Classification Search
None
See application file for complete search history.

(56) References Cited

U.S. PATENT DOCUMENTS

| 6,433,142 | B1 | 8/2002 | Turner et al. |
| 6,743,774 | B1 | 6/2004 | Jay |
| 6,960,562 | B2 | 11/2005 | Jay |
| 7,001,881 | B1 | 2/2006 | Jay |
| 7,030,223 | B2 | 4/2006 | Turner et al. |
| 7,361,738 | B2 | 4/2008 | Turner et al. |
| 7,415,381 | B2 | 8/2008 | Jay |
| 7,618,941 | B2 | 11/2009 | Jay |
| 8,026,346 | B2 | 9/2011 | Jay |
| 8,506,944 | B2 | 8/2013 | Sullivan et al. |
| 8,551,467 | B2 | 10/2013 | Sullivan et al. |
| 8,563,028 | B2 | 10/2013 | Sullivan et al. |
| 8,680,057 | B2 | 3/2014 | Jay |
| 8,945,604 | B2 | 2/2015 | Sullivan et al. |
| 8,980,840 | B2 | 3/2015 | Truitt, III et al. |
| 9,107,885 | B2 | 8/2015 | Sullivan et al. |
| 9,138,457 | B2 | 9/2015 | Sullivan et al. |
| 9,239,409 | B2 | 1/2016 | Qiu et al. |
| 9,248,161 | B2 | 2/2016 | Sullivan et al. |
| 9,393,285 | B2 | 7/2016 | Sullivan et al. |
| 9,421,241 | B2 | 8/2016 | Sullivan et al. |
| 9,585,936 | B2 | 3/2017 | Sullivan et al. |
| 9,730,865 | B2 | 8/2017 | Sullivan et al. |
| 9,730,978 | B2 | 8/2017 | Sullivan et al. |
| 9,974,685 | B2 | 5/2018 | Cadden et al. |
| 9,982,027 | B2 | 5/2018 | Schmidt |
| 10,125,180 | B2 | 11/2018 | Schmidt et al. |
| 10,383,796 | B2 | 8/2019 | Truitt et al. |
| 10,500,250 | B2 | 12/2019 | Jay et al. |
| 10,500,251 | B2 | 12/2019 | Jay et al. |

(Continued)

FOREIGN PATENT DOCUMENTS

| JP | 2011519933 A | 7/2011 |
| WO | WO-2000/064930 A2 | 11/2000 |

(Continued)

OTHER PUBLICATIONS

AG, WaveLight Laser Technologie, and Am Wolfsmantel. "Allegretto Wave." Scanning Spot LASIK Laser System Procedure Manual Information for Professional Use (2002). (Year: 2002).*

Chao, Wendy, et al. "Section: Special Article. David A. Sullivan, PhD, Guest Editor Title: Report of the Inaugural Meeting of the TFOS i2= initiating innovation Series: Targeting the Unmet Need for Dry Eye Treatment (London, United Kingdom, Mar. 21, 2015)." (2015). (Year: 2015).*

Extended European Search Report and Search Opinion for European Patent Application No. 16797292.6 dated Jan. 10, 2019 (8 pages).

(Continued)

*Primary Examiner* — Layla Soroush
(74) *Attorney, Agent, or Firm* — Goodwin Procter LLP (57) ABSTRACT Disclosed are methods involving the therapeutic use of human PRG4 (lubricin) protein, to improve vision, to reduce aberrations such as impaired night vision, halos, and glare, to improve the stability of the tear film, and to homogenize the refractive index of the surface of the eye.

18 Claims, 4 Drawing Sheets

Specification includes a Sequence Listing.

(56) References Cited

U.S. PATENT DOCUMENTS

| | | | |
|---|---|---|---|
| 10,723,773 | B2 | 7/2020 | Schmidt et al. |
| 10,960,047 | B2 | 3/2021 | Jay et al. |
| 10,967,048 | B2 | 4/2021 | Jay et al. |
| 2006/0240037 | A1 | 10/2006 | Fey et al. |
| 2007/0111327 | A1 | 5/2007 | Jay |
| 2007/0249557 | A1 | 10/2007 | Jay |
| 2008/0139458 | A1 | 6/2008 | Jay et al. |
| 2008/0143816 | A1 | 6/2008 | Zhang et al. |
| 2008/0287369 | A1 | 11/2008 | Jay |
| 2009/0068247 | A1 | 3/2009 | Jay |
| 2009/0104148 | A1 | 4/2009 | Jay et al. |
| 2009/0155200 | A1 | 6/2009 | Jay |
| 2010/0092452 | A1 | 4/2010 | Sullivan et al. |
| 2010/0204087 | A1 | 8/2010 | Jay |
| 2011/0059902 | A1 | 3/2011 | Sullivan et al. |
| 2011/0070222 | A1 | 3/2011 | Sullivan et al. |
| 2011/0142908 | A1 | 6/2011 | Sullivan et al. |
| 2012/0321611 | A1 | 12/2012 | Sullivan et al. |
| 2013/0039865 | A1 | 2/2013 | Truitt, III et al. |
| 2013/0116186 | A1 | 5/2013 | Jay |
| 2013/0315973 | A1 | 11/2013 | Jay |
| 2014/0179611 | A1 | 6/2014 | Jay |
| 2016/0250286 | A1 | 9/2016 | Schmidt |
| 2016/0304572 | A1 | 10/2016 | Schmidt et al. |
| 2017/0246246 | A1 | 8/2017 | Jay et al. |
| 2017/0312335 | A1 | 11/2017 | Truitt, III et al. |
| 2018/0015141 | A1 | 1/2018 | Jay et al. |
| 2018/0028598 | A1 | 2/2018 | Sullivan et al. |
| 2018/0161393 | A1 | 6/2018 | Jay et al. |

FOREIGN PATENT DOCUMENTS

| | | |
|---|---|---|
| WO | WO-2008/143816 | 11/2008 |
| WO | WO-2009/137217 A2 | 11/2009 |
| WO | WO-2009/137602 A1 | 11/2009 |
| WO | WO-2010/135736 A2 | 11/2010 |
| WO | WO-2011/019963 A2 | 2/2011 |
| WO | WO-2011/050287 A1 | 4/2011 |
| WO | WO-2011/091000 A2 | 7/2011 |
| WO | WO-2015/060935 A1 | 4/2015 |
| WO | WO-2015/061488 A1 | 4/2015 |

OTHER PUBLICATIONS

Samson, et al., "PRG4 as a Natural Boundary Lubricant for Commerical Silicon Hydogel Contact Lenses", Investigative Ophthalmology & Visual Science, Jun. 2013; 54(5468):1-2.

Samson et al., "Characterization of full-length recombinant human Proteoglycan 4 as an ocular surface boundary lubricant", Experimental Eye Research, 2014; 127: 14-19.

Schmidt et al., "Transcription, Translation, and Function of Lubricin, a Boundary Lubricant, at the Ocular Surface", JAMA Ophthalmol, Jun. 12, 2013; 131(6):1-23.

Lambiase et al., "Randomized, Double-masked Study to Evaluate Safety and Efficacy of Lubricin (150 µg/mL) Eye Drops Versus Sodium Hyaluronate (HA) 0.18% Eye Drops (Vismed) in Patients with Moderate Dry Eye Disease," Ocul Surf. Jan. 2017;15(1):77-87. Epub Sep. 8, 2016.

Campbell, "The effect of tear film on higher order corrections applied to the corneal surface during wavefront-guided refractive surgery," J Refract Surg. Sep.-Oct. 2005;21(5):S519-24. PubMed PMID: 16209454.

Comer et al., (1994), "The Effect of Tear Film Loss on Contrast Sensitivity: Poster # 59 (OR-105)," Optometry and Vision Science, 71(12):176-177.

Denoyer, et al., "Tear film aberration dynamics and vision-related quality of life in patients with dry eye disease," Ophthalmology. Sep. 2012;119(9):1811-8. doi: 10.1016/j.ophtha.2012.03.004. Epub May 15, 2012. PubMed PMID: 22591770.

Deschamps, et al., "The impact of dry eye disease on visual performance while driving," Am J Ophthalmol. Jul. 2013;156(1):184-189.e3. doi: 10.1016/j.ajo.2013.02.019. Epub May 22, 2013. PubMed PMID: 23706501.

Dursun, et al., "The effects of experimental tear film removal on corneal surface regularity and barrier function," Ophthalmology. Sep. 2000;107(9):1754-60. PubMed PMID: 10964840.

Efron, et al., "Repeatability and reliability of ocular aberration measurements in contact lens wear," Cont Lens Anterior Eye. Apr. 2008;31(2):81-8. Epub Dec. 3, 2007. PubMed PMID: 18061516.

Ferrer-Blasco, et al., "Dynamic changes in the air-tear film interface modulation transfer function," Graefes Arch Clin Exp Ophthalmol. Jan. 2010;248(1):127-32. doi: 10.1007/s00417-009-1197-0. Epub Sep. 25, 2009. PubMed PMID: 19779931.

Gartaganis, et al., "Effects of oral acitretin on contrast sensitivity and tear film function: a prospective study," Skin Pharmacol Appl Skin Physiol. May-Jun. 2002;15(3):200-4. PubMed PMID: 12077473.

Himebaugh, et al., "Scale and spatial distribution of aberrations associated with tear breakup," Optom Vis Sci. Nov. 2012;89(11):1590-600. doi: 10.1097/OPX.0b013e31826cfae5. PubMed PMID: 23080060; PubMed Central PMCID: PMC3756908.

Huang, et al., "Effect of artificial tears on corneal surface regularity, contrast sensitivity, and glare disability in dry eyes," Ophthalmology. Oct. 2002;109(10):1934-40. PubMed PMID: 12359618.

Jung, et al., "Higher order aberrations of the corneal surface after laser subepithelial keratomileusis," Korean J Ophthalmol. Aug. 2014;28(4):285-91. doi: 10.3341/kjo.2014.28.4.285. Epub Jul. 22, 2014. PubMed PMID: 25120336; PubMed Central PMCID: PMC4120348.

Koh, et al., "Effect of diquafosol ophthalmic solution on the optical quality of the eyes in patients with aqueous-deficient dry eye," Acta Ophthalmol. Dec. 2014;92(8):e671-5. doi: 10.1111/aos.12443. Epub May 25, 2014. PubMed PMID: 24863298.

Koh, et al., "Effect of rebamipide ophthalmic suspension on optical quality in the short break-up time type of dry eye," Cornea. Sep. 2013;32(9):1219-23. doi: 10.1097/ICO.0b013e318294f97e. PubMed PMID: 23676786.

Koh, et al., "Effects of suppression of blinking on quality of vision in borderline cases of evaporative dry eye," Cornea. Apr. 2008;27(3):275-8. doi: 10.1097/ICO.0b013e31815be9c8. PubMed PMID: 18362651.

Koh, et al., "Serial measurements of higher-order aberrations after blinking in normal subjects," Invest Ophthalmol Vis Sci. Aug. 2006;47(8):3318-24. PubMed PMID: 16877397.

Koh, et al., "Simultaneous measurement of tear film dynamics using wavefront sensor and optical coherence tomography," Invest Ophthalmol Vis Sci. Jul. 2010;51(7):3441-8. doi: 10.1167/iovs.09-4430. Epub Feb. 17, 2010. PubMed PMID: 20164455.

Li, et al., "Changes in aberrations and retinal image quality due to tear film dynamics," Opt Express. Dec. 11, 2006;14(25):12552-9. PubMed PMID: 19529690.

Montés-Micó, et al., "Dynamic changes in the tear film in dry eyes," Invest Ophthalmol Vis Sci. May 2005;46(5):1615-9. PubMed PMID: 15851559.

Montés-Micó, et al., "Optical quality after instillation of eyedrops in dry-eye syndrome," J Cataract Refract Surg. Jun. 2010;36(6):935-40. doi: 10.1016/j.jcrs.2009.12.044. PubMed PMID: 20494764.

Montés-Micó, et al., "Postblink changes in total and corneal ocular aberrations," Ophthalmology. Apr. 2004;111(4):758-67. PubMed PMID: 15051210.

Montés-Micó, et al., "Temporal changes in optical quality of air-tear film interface at anterior cornea after blink," Invest Ophthalmol Vis Sci. Jun. 2004;45(6):1752-7. PubMed PMID: 15161836.

Montés-Micó, et al., "The tear film and the optical quality of the eye," Ocul Surf. Oct. 2010;8(4):185-92. Review. PubMed PMID: 20964981.

Montés-Micó, et al., "Wavefront analysis of higher order aberrations in dry eye patients", J Refract Surg. May-Jun. 2004;20(3):243-7. PubMed PMID: 15188901.

Rae, et al., "The effect of soft contact lens wear and time from blink on wavefront aberration measurement variation," Clin Exp Optom. May 2009;92(3):274-82. doi: 10.1111/j.1444-0938.2009.00377.x. Epub Apr. 1, 2009. PubMed PMID: 19351377.

Ridder, et al., "Contrast sensitivity and tear layer aberrometry in dry eye patients," Optom Vis Sci. Sep. 2009;86(9):E1059-68. doi: 10.1097/OPX.0b013e3181b599bf. PubMed PMID: 19648840.

(56) References Cited

OTHER PUBLICATIONS

Ridder, et al., "Effect of artificial tears on visual performance in subjects with dry eye," Optom Vis Sci. Sep. 2005;82(9):835-42. PubMed PMID: 16189494.
Ridder, et al., "Short-term effects of artificial tears on visual performance in normal subjects," Optom Vis Sci. May 2005;82(5):370-7. PubMed PMID: 15894913.
Ridder, et al., "The effect of artificial tears on visual performance in normal subjects wearing contact lenses," Optom Vis Sci. Dec. 2003;80(12):826-31. PubMed PMID: 14688546.
Rieger, "Color discrimination in patients with keratoconjunctivitis sicca before and after artificial tear application," Wien Klin Wochenschr. Apr. 24, 1998;110(8):296-7. PubMed PMID: 9615962.
Rieger, "Contrast sensitivity in patients with keratoconjunctivitis sicca before and after artificial tear application," Graefes Arch Clin Exp Ophthalmol. Oct. 1993;231(10):577-9. PubMed PMID: 8224932.
Rolando, et al., "Low spatial-contrast sensitivity in dry eyes," Cornea. Jul. 1998;17(4):376-9. PubMed PMID: 9676908.
Thai, et al., "Contact lens drying and visual performance: the vision cycle with contact lenses," Optom Vis Sci. Jun. 2002;79(6):381-8. PubMed PMID: 12086305.
Tutt, et al., "Optical and visual impact of tear break-up in human eyes," Invest Ophthalmol Vis Sci. Dec. 2000;41(13):4117-23. PubMed PMID: 11095604.
Wang, et al., "Dynamic wavefront aberrations and visual acuity in normal and dry eyes," Clin Exp Optom. May 2009;92(3):267-73. PubMed PMID: 19469018.
Cataract, Merck Manuals [retrieved from internet on Sep. 20, 2007] http://web.archive.org/web/20150418063508/http://www.merckmanuals.com/profession al/eye-disorders/cataract/cataract> published on Apr. 18, 2015 as per Wayback Machine.
Cataracts Symptoms [retrieved from internet on Sep. 20, 2007] <URL:http://http://web.archive.org/web/20150507081543/http://www.mayoclinic.org/diseasesconditions/cataracts/basics/symptoms/con-20015113> published on May 7, 2015 as per Wayback Machine.
Flannery et al., "Prevention of Cartilage Degeneration in a Rat Model of Osteoarthritis by Intraarticular Treatment With Recombinant Lubricin", Arthritis Rheum, 2009, 60(3):804-7.
Harvey,JE, et al, "Total integrated scatter from surfaces with arbitrary roughness, correlation widths, and incident angles", Optical Engineering, 2012, 51(1), 013402: 1-11.
International Search Report for International Application No. PCT/US2016/033248, dated Jun. 27, 2016 (7 pages).

Jay et al., "Boundary Lubrication by Lubricin is Mediated by O-Linked Beta(1-3)Gal-GalNAc Oligosaccharides", 2001, Glycoconj. J. 18:807-815.
King-Smith et al, "Tear Film Interferometry and Corneal Surface Roughness", Invest Ophthalmol Vis. Sci, Apr. 21, 2014, 55(4):2614-8.
Mamalis N., Laser vision correction among physicians: "The proof of the pudding is in the eating". J Cataract Refract Surg. Mar. 2014; 40(3):343-4.
Visual Acuity, Wikipedia [retrieved from internet on Sep. 20, 2007] <URL:http://web.archive.org/web/20150506193820/http://en.wikipedia.org/wiki/Visual_acuity> published on May 6, 2015 as per Wayback Machine.
Written Opinion of the International Searching Authority for International Patent Application No. PCT/US2016/033248, dated Jun. 27, 2016 (4 pages).
"Dry Eye and Visual Performance" from Frontiers in Dry Eye, 2011, 6(1):22-29 (in Japanese with an English Translation of p. 22, 2nd ¶ through to the 1st ¶ on p. 23 in the left hand column provided).
"Japan Ophthalmologists Association, 'Handbook for Proper Use of Ophthalmic Solutions—Questions and Answers,'" 1st edition, (2011), p. 1-20, (<https://www.rad-ar.or.jp/use/basis/pdf/meausuri02.pdf>) (in Japanese with an English Translation of Question 1 (p. 4, lines 2 to 9) provided).
Aragona et al., (2019), "Physicochemical Properties of Hyaluronic Acid-Based Lubricant Eye Drops," *TVST*, 8(6):Article 2.
Jones et al., (2017), "TFOS DEWS II Management and Therapy Report," 15(3): 575-628.
Lievens et al. (2019), "Evaluation of an enhanced viscosity artificial tear for moderate to severe dry eye disease: a multicenter, double-masked, randomized 30-day study," *Contact Lens and Anterior Eye*, 42:443-449.
Berger et al., (2009), "Comparison of two artificial tear formulations using aberrometry," *Clinical and Experimental Optometry*, 92(3):206-211.
Vessel, (2017), "Higher Order Aberrations," accessed in 2020 from https://www.allaboutvision.com/conditions/aberrations.htm (6 pages).
Wade, (2015), "Symptoms of Dry Eye Disease," Aug. 18, 2015, accessed at https://discoveryeye.org/symptoms-of-dry-eye-disease/ (6 pages).
Koh, Shizuka, (2011) "Dry Eye, Higher Order Aberrations and Impaired Visual Performance—Optical Quality in Dry Eye", Ophthalmology, 53,(11):1567-1574 (Japanese Language Reference with English translation of selected passages).

\* cited by examiner

FIGS. 1A-C

1A. Unstable Tear Film; Blink #1

1B. Unstable Tear Film; Blink #2

1C. Tear Film After PRG4 Administration

FIG. 2

SEQ ID NO: 1, LENGTH: 1404, ORGANISM: Homo sapiens, UniProt Accession No. Q92954:

MAWKTLPIYL LLLLSVFVIQ QVSSQDLSSC AGRCGEGYSR DATCNCDYNC QHYMECCPDF
KRVCTAELSC KGRCFESFER GRECDCDAQC KKYDKCCPDY ESFCAEVHNP TSPPSSKKAP
PPSGASQTIK STTKRSPKPP NKKKTKKVIE SEEITEEHSV SENQESSSSS SSSSSSSTIR
KIKSSKNSAA NRELQKKLKV KDNKKNRTKK KPTPKPPVVD EAGSGLDNGD FKVTTPDTST
TQHNKVSTSP KITTAKPINP RPSLPPNSDT SKETSLTVNK ETTVETKETT TTNKQTSTDG
KEKTTSAKET QSIEKTSAKD LAPTSKVLAK PTPKAETTTK GPALTTPKEP TPTTPKEPAS
TTPKEPTPTT IKSAPTTPKE PAPTTTKSAP TTPKEPAPTT TKEPAPTTPK EPAPTTTKEP
APTTTKSAPT TPKEPAPTTP KKPAPTTPKE PAPTTPKEPT PTTPKEPAPT TKEPAPTTPK
EPAPTAPKKP APTTPKEPAP TTPKEPAPTT TKEPSPTTPK EPAPTTTKSA PTTTKEPAPT
TTKSAPTTPK EPSPTTTKEP APTTPKEPAP TTPKKPAPTT PKEPAPTTPK EPAPTTTKKP
APTTPKEPAP TTPKETAPTT PKKLTPTTPE KLAPTTPEKP APTTPEELAP TTPEEPTPTT
PEEPAPTTPK AAAPNTPKEP APTTPKEPAP TTPKEPAPTT PKETAPTTPK GTAPTTLKEP
APTTPKKPAP KELAPTTTKE PTSTTCDKPA PTTPKGTAPT TPKEPAPTTP KEPAPTTPKG
TAPTTLKEPA PTTPKKPAPK ELAPTTTKGP TSTTSDKPAP TTPKETAPTT PKEPAPTTPK
KPAPTTPETP PPTTSEVSTP TTTKEPTTIH KSPDESTPEL SAEPTPKALE NSPKEPGVPT
TKTPAATKPE MTTTAKDKTT ERDLRTTPET TTAAPKMTKE TATTTEKTTE SKITATTTQV
TSTTTQDTTP FKITTLKTTT LAPKVTTTKK TITTTEIMNK PEETAKPKDR ATNSKATTPK
PQKPTKAPKK PTSTKKPKTM PRVRKPKTTP TPRKMTSTMP ELNPTSRIAE AMLQTTTRPN
QTPNSKLVEV NPKSEDAGGA EGETPHMLLR PHVFMPEVTP DMDYLPRVPN QGIIINPMLS
DETNICNGKP VDGLTTLRNG TLVAFRGHYF WMLSPFSPPS PARRITEVWG IPSPIDTVFT
RCNCEGKTFF FKDSQYWRFT NDIKDAGYPK PIFKGFGGLT GQIVAALSTA KYKNWPESVY
FFKRGGSIQQ YIYKQEPVQK CPGRRPALNY PVYGETTQVR RRFERAIGP SQTHTIRIQY
SPARLAYQDK GVLHNEVKVS ILWRGLPNVV TSAISLPNIR KPDGYDYYAF SKDQYYNIDV
PSRTARAITT RSGQTLSKVW YNCP

FIG. 3A

Residues 1-2560 of SEQ ID NO: 2 LENGTH: 5041, TYPE: DNA,
ORGANISM: Homo sapiens, GenBank Accession No. U70136.1:

GCGGCCGCGACTATTCGGTACCTGAAAACAACGATGGCATGGAAAACACTTCCCATTTACCTGT
TGTTGCTGCTGTCTGTTTTCGTGATTCAGCAAGTTTCATCTCAAGATTTATCAAGCTGTGCAGG
GAGATGTGGGGAAGGGTATTCTAGAGATGCCACCTGCAACTGTGATTATAACTGTCAACACTAC
ATGGAGTGCTGCCCTGATTTCAAGAGAGTCTGCACTGCGGAGCTTTCCTGTAAAGGCCGCTGCT
TTGAGTCCTTCGAGAGAGGGAGGGAGTGTGACTGCGACGCCCAATGTAAGAAGTATGACAAGTG
CTGTCCCGATTATGAGAGTTTCTGTGCAGAAGTGCATAATCCCACATCACCACCATCTTCAAAG
AAAGCACCTCCACCTTCAGGAGCATCTCAAACCATCAAATCAACAACCAAACGTTCACCCAAAC
CACCAAACAAGAAGAAGACTAAGAAAGTTATAGAATCAGAGGAAATAACAGAAGAACATTCTGT
TTCTGAAAATCAAGAGTCCTCCTCCTCCTCCTCCTCTTCCTCTTCTTCTTCAACAATTTGGAAA
ATCAAGTCTTCCAAAAATTCAGCTGCTAATAGAGAATTACAGAAGAAACTCAAAGTAAAAGATA
ACAAGAAGAACAGAACTAAAAGAAACCTACCCCCAAACCACCAGTTGTAGATGAAGCTGGAAG
TGGATTGGACAATGGTGACTTCAAGGTCACAACTCCTGACACGTCTACCACCCAACACAATAAA
GTCAGCACATCTCCCAAGATCACAACAGCAAAACCAATAAATCCCAGACCCAGTCTTCCACCTA
ATTCTGATACATCTAAAGAGACGTCTTTGACAGTGAATAAAGAGACAACAGTTGAAACTAAAGA
AACTACTACAACAAATAAACAGACTTCAACTGATGGAAAAGAGAAGACTACTTCCGCTAAAGAG
ACACAAAGTATAGAGAAAACATCTGCTAAAGATTTAGCACCCACATCTAAAGTGCTGGCTAAAC
CTACACCCAAAGCTGAAACTACAACCAAAGGCCCTGCTCTCACCACTCCCAAGGAGCCCACGCC
CACCACTCCCAAGGAGCCTGCATCTACCACACCCAAAGAGCCCACACCTACCACCATCAAGTCT
GCACCCACCACCCCCAAGGAGCCTGCACCCACCACCACCAAGTCTGCACCCACCACTCCCAAGG
AGCCTGCACCCACCACCACCAAGGAGCCTGCACCCACCACTCCCAAGGAGCCTGCACCCACCAC
CACCAAGGAGCCTGCACCCACCACCACCAAGTCTGCACCCACCACTCCCAAGGAGCCTGCACCC
ACCACCCCAAGAAGCCTGCCCCAACTACCCCCAAGGAGCCTGCACCCACCACTCCCAAGGAGC
CTACACCCACCACTCCCAAGGAGCCTGCACCCACCACCAAGGAGCCTGCACCCACCACTCCCAA
AGAGCCTGCACCCACTGCCCCAAGAAGCCTGCCCCAACTACCCCCAAGGAGCCTGCACCCACC
ACTCCCAAGGAGCCTGCACCCACCACCACCAAGGAGCCTTCACCCACCACTCCCAAGGAGCCTG
CACCCACCACCACCAAGTCTGCACCCACCACTACCAAGGAGCCTGCACCCACCACTACCAAGTC
TGCACCCACCACTCCCAAGGAGCCTTCACCCACCACCACCAAGGAGCCTGCACCCACCACTCCC
AAGGAGCCTGCACCCACCACCCCCAAGAAGCCTGCCCCAACTACCCCCAAGGAGCCTGCACCCA
CCACTCCCAAGGAACCTGCACCCACCACCACCAAGAAGCCTGCACCCACCGCTCCCAAAGAGCC
TGCCCCAACTACCCCCAAGGAGACTGCACCCACCACCCCCAAGAAGCTCACGCCCACCACCCCC
GAGAAGCTCGCACCCACCACCCCTGAGAAGCCCGCACCCACCACCCCTGAGGAGCTCGCACCCA
CCACCCCTGAGGAGCCCACACCCACCACCCCTGAGGAGCCTGCTCCCACCACTCCCAAGGCAGC
GGCTCCCAACACCCCTAAGGAGCCTGCTCCAACTACCCCTAAGGAGCCTGCTCCAACTACCCCT
AAGGAGCCTGCTCCAACTACCCCTAAGGAGACTGCTCCAACTACCCCTAAAGGGACTGCTCCAA
CTACCCTCAAGGAACCTGCACCCACTACTCCCAAGAAGCCTGCCCCAAGGAGCTTGCACCCAC
CACCACCAAGGAGCCCACATCCACCACCTCTGACAAGCCCGCTCCAACTACCCCTAAGGGGACT
GCTCCAACTACCCCTAAGGAGCCTGCTCCAACTACCCCTAAGGAGCCTGCTCCAACTACCCCTA
AGGGGACTGCTCCAACTACCCTCAAGGAACCTGCACCCACTACTCCCAAGAAGCCTGCCCCCAA
GGAGCTTGCACCCACCACCACCAAGGGGCCCACATCCACCACCTCTGACAAGCCTGCTCCAACT
ACACCTAAGGAGACTGCTCCAACTACCCCCAAGGAGCCTGCACCCACTACCCCCAAGAAGCCTG

FIG. 3B

Residues 2561-5041 of SEQ ID NO: 2 LENGTH: 5041, TYPE: DNA, ORGANISM: Homo sapiens, GenBank Accession No. U70136.1:

```
CTCCAACTACTCCTGAGACACCTCCTCCAACCACTTCAGAGGTCTCTACTCCAACTACCACCAA
GGAGCCTACCACTATCCACAAAAGCCCTGATGAATCAACTCCTGAGCTTTCTGCAGAACCCACA
CCAAAAGCTCTTGAAAACAGTCCCAAGGAACCTGGTGTACCTACAACTAAGACTCCTGCAGCGA
CTAAACCTGAAATGACTACAACAGCTAAAGACAAGACAACAGAAAGAGACTTACGTACTACACC
TGAAACTACAACTGCTGCACCTAAGATGACAAAAGAGACAGCAACTACAACAGAAAAAACTACC
GAATCCAAAATAACAGCTACAACCACACAAGTAACATCTACCACAACTCAAGATACCACACCAT
TCAAAATTACTACTCTTAAAACAACTACTCTTGCACCCAAAGTAACTACAACAAAAAAGACAAT
TACTACCACTGAGATTATGAACAAACCTGAAGAAACAGCTAAACCAAAAGACAGAGCTACTAAT
TCTAAAGCGACAACTCCTAAACCTCAAAAGCCAACCAAAGCACCCAAAAAACCCACTTCTACCA
AAAAGCCAAAAACAATGCCTAGAGTGAGAAAACCAAAGACGACACCAACTCCCCGCAAGATGAC
ATCAACAATGCCAGAATTGAACCCTACCTCAAGAATAGCAGAAGCCATGCTCCAAACCACCACC
AGACCTAACCAAACTCCAAACTCCAAACTAGTTGAAGTAAATCCAAAGAGTGAAGATGCAGGTG
GTGCTGAAGGAGAAACACCTCATATGCTTCTCAGGCCCCATGTGTTCATGCCTGAAGTTACTCC
CGACATGGATTACTTACCGAGAGTACCCAATCAAGGCATTATCATCAATCCCATGCTTTCCGAT
GAGACCAATATATGCAATGGTAAGCCAGTAGATGGACTGACTACTTTGCGCAATGGGACATTAG
TTGCATTCCGAGGTCATTATTTCTGGATGCTAAGTCCATTCAGTCCACCATCTCCAGCTCGCAG
AATTACTGAAGTTTGGGGTATTCCTTCCCCCATTGATACTGTTTTACTAGGTGCAACTGTGAA
GGAAAAACTTTCTTCTTTAAGGATTCTCAGTACTGGCGTTTTACCAATGATATAAAAGATGCAG
GGTACCCCAAACCAATTTTCAAAGGATTTGGAGGACTAACTGGACAAATAGTGGCAGCGCTTTC
AACAGCTAAATATAAGAACTGGCCTGAATCTGTGTATTTTTTCAAGAGAGGTGGCAGCATTCAG
CAGTATATTTATAAACAGGAACCTGTACAGAAGTGCCCTGGAAGAAGGCCTGCTCTAAATTATC
CAGTGTATGGAGAAATGACACAGGTTAGGAGACGTCGCTTTGAACGTGCTATAGGACCTTCTCA
AACACACACCATCAGAATTCAATATTCACCTGCCAGACTGGCTTATCAAGACAAAGGTGTCCTT
CATAATGAAGTTAAAGTGAGTATACTGTGGAGAGGACTTCCAAATGTGGTTACCTCAGCTATAT
CACTGCCCAACATCAGAAAACCTGACGGCTATGATTACTATGCCTTTTCTAAAGATCAATACTA
TAACATTGATGTGCCTAGTAGAACAGCAAGAGCAATTACTACTCGTTCTGGGCAGACCTTATCC
AAAGTCTGGTACAACTGTCCTTAGACTGATGAGCAAGGAGGAGTCAACTAATGAAGAAATGAA
TAATAAATTTTGACACTGAAAAACATTTTATTAATAAAGAATATTGACATGAGTATACCAGTTT
ATATATAAAAATGTTTTTAAACTTGACAATCATTACACTAAAACAGATTTGATAATCTTATTCA
CAGTTGTTATTGTTTACAGACCATTTAATTAATATTTCCTCTGTTTATTCCTCCTCTCCCTCCC
ATTGCATGGCTCACACCTGTAAAAGAAAAAGAATCAAATTGAATATATCTTTTAAGAATTCAA
AACTAGTGTATTCACTTACCCTAGTTCATTATAAAAAATATCTAGGCATTGTGGATATAAAACT
GTTGGGTATTCTACAACTTCAATGGAAATTATTACAAGCAGATTAATCCCTCTTTTGTGACAC
AAGTACAATCTAAAAGTTATATTGGAAAACATGGAAATATTAAAATTTTACACTTTTACTAGCT
AAAACATAATCACAAAGCTTTATCGTGTTGTATAAAAAAATTAACAATATAATGGCAATAGGTA
GAGATACAACAAATGAATATAACACTATAACACTTCATATTTTCCAAATCTTAATTTGGATTTA
AGGAAGAAATCAATAAATATAAAATATAAGCACATATTTATTATATATCTAAGGTATACAAATC
TGTCTACATGAAGTTTACAGATTGGTAAATATCACCTGCTCAACATGTAATTATTTAATAAAAC
TTTGGAACATTAAAAAAATAAATTGGAGGCTTAAAAAAAAAAAAAAAAA
```

USE OF PRG4 TO IMPROVE DYNAMIC VISUAL ACUITY AND HIGHER ORDER ABERRATIONS

CROSS-REFERENCE TO RELATED APPLICATIONS

This application is a U.S. National Stage Application filed under 35 U.S.C. § 371 of International Patent Application No. PCT/US2016/033248, filed May 19, 2016, which claims priority to and the benefit of U.S. Provisional Patent Application No. 62/163,753 filed May 19, 2015, the contents of each of which are incorporated by reference herein in their entireties.

BACKGROUND OF THE INVENTION

This invention relates to new vision therapies exploiting solutions of lubricin, or PRG4. More particularly, it relates to use of lubricin-containing eye drops for improving static and dynamic visual acuity, reducing vision halos and starbursts, diminishing glare, diminishing coma, spherical, or trefoil aberration, improving night vision, and/or stabilize the tear film to prevent or limit degradation of its optical lensing function between blinks.

The proteoglycan 4 (PRG4) gene encodes a highly glycosylated proteins now known as lubricin. Lubricin originally was identified as an expression product of synovial fibroblasts and shown to possess boundary lubricating ability by Jay et al. O-linked beta (1-3) Gal-GalNAc oligosaccharides pendant from a large central mucin-like domain of 940 amino acids encoded by exon 6 of the PRG4 gene subsequently were shown to be critical to the molecule's boundary lubricating ability. Lubricin has been shown to contribute to the boundary lubrication of apposing articular cartilage surfaces. More recently, lubricin has been discovered to be useful in the eye, for the treatment of dry eye disease, as a coating for a contact or intraocular lens to improve comfort and maintain uncontaminated exploiting its anti-adhesive effects, and as a component of a solution for cleaning or storing a contact lens. The function of PRG4 heretofore has been almost entirely associated with prevention of wear between articulating joints and lubrication of interfacing tissues such as between the surface of the eye and eyelid. See, for example, U.S. Patent Application Publication Nos. 2009/0068247, 2010/0092452, 2011/0059902, 2011/0070222, 2011/0142908, and 2012/0321611.

Deterioration or impairment of vision occurs through aging, injury, irritation, and many unknown factors related to genetics. Of course, enormous vision improvements are routinely achieved through the use of corrective lenses, and in the last 40 years or so increasingly by various surgical procedures. Laser in-situ keratomileusis (LASIK surgery), involves surgical creation of a flap across the central portion of the cornea, and beneath this epithelial flap reshaping the cornea using a laser to improve the way light passes through the eye. Once the reshaping is complete, the flap is set down to heal. LASIK reshapes the underlying corneal stroma but does not modify the epithelium, excepting any residual ridges from the flap interface healing. Photorefractive keratectomy surgery (PRK) is used to correct mild to moderate nearsightedness, farsightedness, and/or astigmatism. During PRK surgery, the epithelium is fully abraded and removed prior to an excimer laser ablation of the stroma, followed by a healing period where the epithelium is encouraged to grow back over the reshaped stomal surface. In laser epithelial keratomileusis (LASEK), an epithelial flap is created by loosening epithelial cells using an alcohol solution, pulling the flap back prior to excimer reshaping of the stroma, then replacing and securing the flap with a soft contact lens while it heals. Cataract surgery involves replacement of a patient's cloudy natural lens with a synthetic lens to restore the lens's transparency. Refractive lens exchange (RLE) is similar to cataract surgery and involves making a small incision at the edge of the cornea to remove the natural lens of the eye and replacing it with a silicone or plastic lens. Presbyopic lens exchange (PRELEX), is a procedure in which a multifocal lens is implanted to correct presbyopia, a condition in which the eye's lens loses its flexibility.

None of these solutions to correct vision impairment or aberrations due to the epithelium or any optical dysfunction caused by the tear film, and none is guaranteed to correct vision perfectly. Rather, each of these procedures carry a non-negligible risk that the epithelium and tear film are compromised following surgery. All of these surgical approaches have limitations or varying frequencies of adverse side effects. For example, wearers of corrective contact lenses often report irritation and loss of visual acuity and clarity after a day of contact lens wear. Eye surgery patients can suffer from starbursts, excessive glare, and issues with low-light, low contrast, and especially night vision. One report suggests that the visual acuity of one out of every five patients is worse after LASIK than the pre surgical acuity corrected with glasses. Halos are smudges of light or rings that appear around luminous or bright objects. They can be around a light itself or around some object that is bright relative to its surroundings, such as a yield or stop sign at night. Halos are distinct from other aberrations that may be faced following eye surgery, such as glare and starbursts, though these all tend to be interrelated. One large retrospective study of LASIK patients found that halos were reported by 30%, glare by 27%, and starbursts by 25%. (Bailey et al, 2003) A survey of physicians who underwent laser eye surgery from 2000 to 2012, exposed post-surgical adverse effects reported by physician-respondents: "glare (43%), halos (41%), and trouble seeing in dim light (35.2%)." Mamalis N., Laser vision correction among physicians: "the proof of the pudding is in the eating". J Cataract Refract Surg. 2014 March; 40(3):343-4. Fully 19% of patients enrolled in an FDA clinical trial for LASIK using the latest technology reported worse or significantly worse "night driving difficulty" six months after surgery. Patients are known to suffer from dysphotopsia following cataract surgery, and from coma, spherical, or trefoil aberration following wavefront-optimized LASIK, often towards the end of an inter-blink period. Common higher order aberrations include vertical prism, horizontal prism, astigmatism, defocus, trefoil, vertical coma, horizontal coma, quadrafoil, secondary astigmatism, spherical aberration, or other aberrations described by higher order Zernike polynomials, as well as generalized micro- or macro-aberrations. These aberrations are generally described by the broadening of the point spread function of the eye.

Such visual impairments are believed to be due in part to inconsistent vision correction across the cornea, to an unstable tear film, various corneal epitheliopathies, dry eye disease, and to corneal swelling. As the pupil dilates, the optical quality of the eye worsens when ocular surface irregularities overlap the ocular aperture. A large pupil makes any uncorrected refractive error more apparent and introduces a variety of aberrations. This leads to the perception of glare and halos around headlights and streetlights. Nighttime glare and halos may also occur if the pupil dilates beyond the area of laser treatment in low light conditions, or if the laser ablation is centered improperly on the eye. When either of these exists, light can bend irregularly at the junction between the treated and untreated cornea. Halo and coma-like effects and other aberrations can affect and interfere with night driving, loss of contrast sensitivity, double vision and poor reading ability, especially in patients who have big pupils in dark conditions. Visual acuity is defined as the sharpness of vision, typically measured by the ability to discern letters or numbers at a given distance according to a fixed standard. Dynamic visual acuity refers to the ability to discriminate these fine details over time, specifically as it relates to the stability of the image across the inter-blink interval.

SUMMARY OF THE INVENTION

It has now been discovered that lubricin can improve quality of vision by smoothing out and homogenizing the refractive index of the tear film, the initial lensing surface of the eye, and by stabilizing the tear film between blinks. The lubricin-ocular surface interaction is a novel mechanism that can contribute to improved vision and can extend and exploit lubricin's function beyond its well-known boundary lubricating and mechanical properties. Lubricin can therefore be used in a number of novel ways in therapeutic contexts to improve vision via its effect on the corneal surface and improvement of tear film stability. Lubricin drops have multiple beneficial effects on the quality of a patient's vision, including improved static and dynamic visual acuity, reduction in halos and starbursts, diminished glare, improved night vision, and reduction or elimination of various higher order aberrations such as vertical prism, horizontal prism, astigmatism, defocus, trefoil, vertical coma, horizontal coma, quadrafoil, secondary astigmatism, spherical aberration, and micro- and macro-aberrations. The drops may be used by persons suffering from any of these visual aberrations, whether caused by a surgical procedure, an eye injury, eye irritation, or a consequence of natural deterioration of vision parameters. The effects are achieved by topical administration of lubricin to the surface of the eye in an amount sufficient to homogenize the refractive index of the corneal surface and to stabilize the tear film to prevent or limit degradation of its optical lensing function during the time interval between blinks.

Accordingly, in one embodiment, the invention provides a method of treating a patient suffering from a visual aberration such as visual halos, visual starbursts, visual glare, loss of static or dynamic visual acuity, or diminished night vision. The method comprising the step of depositing onto the surface of one or both eyes of the patient an amount of an ophthalmically acceptable solution comprising lubricin sufficient to form a film of lubricin across the corneal surface of the eye or eyes and to alleviate the visual aberration. The film may be of a thickness and mass sufficient to stabilize the tear film, to prevent or limit degradation of its optical lensing function, or to stabilize and homogenize its refractive index. The method also may be used to treat patients suffering from higher order visual aberrations such as vertical prism, horizontal prism, astigmatism, defocus, trefoil, vertical coma, horizontal coma, quadrafoil, secondary astigmatism, spherical aberration, micro- and macro-aberrations, or other aberrations described by Zernike polynomials. The method also can treat unstable vision, particularly with increasing higher order aberrations over time between blinks, by in this case depositing onto the surface of one or both an amount of an ophthalmically acceptable lubricin solution sufficient both to form a film of lubricin across the corneal surface of the eye or eyes and to alleviate the time-varying visual aberrations. The invention permits treatment of patients suffering from these aberrations who have had prior eye surgery such as cataract surgery, laser in-situ keratomileusis (LASIK), photorefractive keratectomy (PRK), laser epithelial keratomileusis (LASEK), refractive lens exchange (RLE) and presbyopic lens exchange (PRELEX).

In preferred embodiments, the method comprises depositing the lubricin as one or more drops of solution having a volume of 10 to 100 microliters, preferably 15 to 30 microliters.

In preferred embodiments, the method comprising depositing the lubricin as a solution having a concentration within the range of 5 µg/mL to 5,000 µg/mL, 10 µg/mL to 300 µg/mL, or 50 µg/mL to 200 µg/mL. The lubricin solution may also include an ophthalmically acceptable surface active phospholipid such as L-α-dipalmitoylphosphatidylcholine, phosphatidylcholine, phosphatidylethanolamine and sphingomyelin, a phosphate buffered saline solution comprising at least sodium phosphate and sodium chloride, an ophthalmically acceptable balanced salt solution comprising one or more electrolytes such as potassium chloride, sodium bicarbonate, potassium bicarbonate, calcium chloride, magnesium chloride, sodium citrate, hydrochloric acid, and sodium hydroxide. The lubricin solution may also include a hyaluronate salt or hyaluronic acid.

In one aspect, the method is practiced on patients who have not been diagnosed with dry eye disease.

In another aspect the invention provides lubricin glycoprotein for the preparation of a medicament for topical application to the human eye of a patient suffering from visual halos, visual starbursts, visual glare, loss of static or dynamic visual acuity, diminished night vision or higher order visual aberrations caused in whole or in part by a defective tear film.

Lubricin drops may be contraindicated for eye surgery patients suffering from an as yet open, or unhealed corneal or other wound (such as a fresh LASIK incision or PRK abradement) as lubricin's anti adhesive properties may interfere with proper healing.

BRIEF DESCRIPTION OF THE DRAWINGS

FIGS. 1A-C are illustrations of the effect an irregular and unstable ocular surface film has on vision, represented by the impact of a variable tear film on the focus of incoming, parallel light rays.

FIG. 2 is the full length lubricin amino acid sequence, showing the secretion signal (first 24 amino acids which are removed during post translational processing).

FIGS. 3A-B provide the full length human DNA encoding lubricin (SEQ ID NO:2). The sequence begins in FIG. 3A which provides residues 1-2560 of SEQ ID NO:2 and concludes in FIG. 3B which provides residues 2561-5041 of SEQ ID NO:2.

DETAILED DESCRIPTION OF THE INVENTION

Figure 1A:
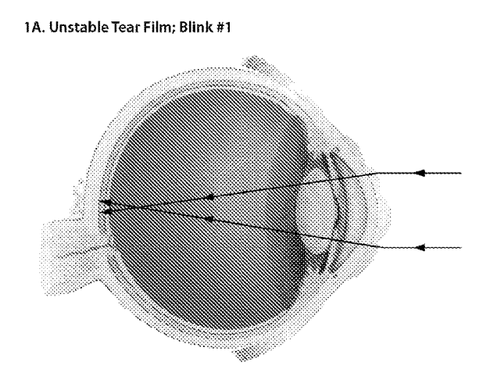
FIG. 1A represents the focus after a first blink.
Figure 1B:
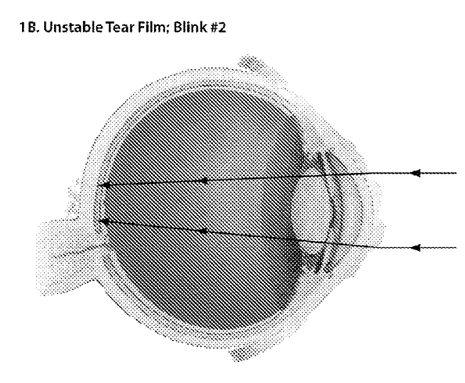
FIG. 1B represents a different focus after a second blink caused by a change in the unstable tear film.
Figure 1C:
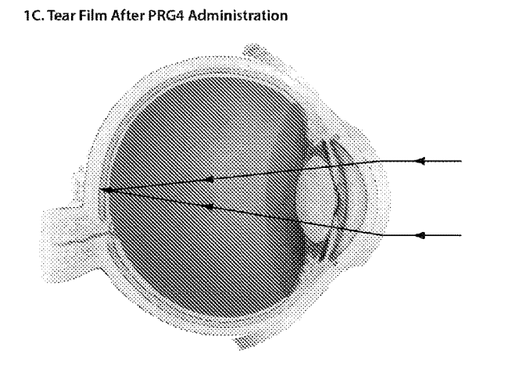
FIG. 1C represents the effect of a topically applied lubricin that homogenizes the refractive index of the tear film on the ocular surface and stabilizes it over time to improve vision and remove higher order aberrations.

The film on the human eye, or tear film, comprises a fluid covering the exposed ocular surface. It is essential for the health and normal function of the eye and visual system. Recent work suggests it comprises a network of mucins disposed in an aqueous body of tear covered by lipids. The various components of the tear system are highly interdependent such that any abnormality in quantity or quality can cause an imbalance in the system and affect vision. Because light must pass through the tear film before it reaches the cornea and deeper posterior eye structures, it may be appreciated that it functions as the "first lens" of the eye.

The present invention provides methods of alleviating vision abnormalities suffered by patients by depositing lubricin on the eye surface to positively affect the tear film's light transmissive properties. Without wishing to be bound, in summary, it is hypothesized that lubricin works to improve vision by stabilizing the tear film (providing lens consistency over time), and homogenizing the refractive index of the ocular surface (providing lens consistency over space) by creating a network of hydrophilic polymer brushes that extend a hydrated layer past the diffraction limit of visible light (a few hundred nm).

Lubricin and the Ocular Surface

The tear film is the first refractive interface between air and water in the eye. It is generally thought to comprise an external lipid layer on the order of 50 nm thick, a middle aqueous layer with varying, time-sensitive estimates on the order of 1-8 µm, and an epithelial interfacial layer comprising the glycocalyx-rich microplicae and microvilli riding atop the corneal surface, estimated to be about 129 nanometers high, with an 95% confidence interval range of about 500 nanometers—including the difference in surface height between cells (King-Smith et al., Invest Ophthalmol Vis Sci., 2014, Apr. 21; 55(4):2614-8). For a normally incident light, the total reflected radiant power function as described by Harvey J E et al. (Optical Engineering 2012, 51(1): 013402; 1-11) is $1-\exp(-(4\pi\sigma/\lambda)^2)$, where $\sigma$ is the RMS roughness of the surface and $\lambda$ is the wavelength of light. An additional approximation, the Rayleigh criterion for smoothness, suggests that a surface may be considered as smooth if the standard deviation of the roughness $h<\lambda/(8 \cos \theta)$, where $\theta$ is the angle of incidence. As the surface roughness of the cornea is on the order of the wavelengths of visible light, the lack of a glycocalyx or the loss of superficial epithelial cells (exposing the immature, hydrophobic, glycocalyx-deficient basal cells beneath) will contribute to an irregular ocular surface and significantly increased scattering in both of these approximations.

Without wishing to be bound, the following is what the inventors suggest is the explanation for lubricin's vision improving properties. Although never measured directly, there is speculation that the glycocalyx may have a higher refractive index than the corneal epithelium, which may bend light preferentially as compared to the other layers. Note that the focal length of a lens (0 is determined by its refractive index (n) and curvature where $1/f=(n-1)(1/R1-1/R2)$, where R1 and R2 represent the semi-major and semi-minor radii of curvature. Local changes in radii or refractive index will change the focal length and create sub-optimal alterations in focus. In addition, the tear film is a dynamic system, especially when compromised. As evaporation is a constant input to the tear film dynamics, the thickness changes as the eye is held open between blinks. Normal, healthy subjects can typically hold their eyes open for well over ten to twenty seconds before the breakup and critical evaporation of the thin film triggers an uncomfortably high osmolarity that triggers a restorative blink. After blinking, the upper lid draws sufficient fluid from the lower tear meniscus over the hydrophilic corneal surface to reform a patent, smooth optical lens at a homeostatic concentration. In conditions where either the tear film has become unstable or the corneal surface has been compromised, the thickness and continuity of the tear film is rapidly degraded, sometimes instantaneously after a blink. This can happen as a natural progression of eye disease (where inflammation or friction cause a glycocalyx-deficient, hyperosmolar corneal epitheliopathy), or following refractive or cataract surgery where incisions into the ocular surface induce scarring or an irregular healing pattern on the ocular surface. In these situations, the normally stable, robust tear film becomes a meta-stable or chaotic system that results in an spatially and temporally unpredictable optical lens. People with these conditions will see different images projected on to their retina from blink-to-blink, causing frustrating variable focus. In order to compensate, these individuals often increase blink rate as they search for a stable image. Breakup may also be anisotropic across the ocular surface, with the resultant irregularity leading to significant, dynamically changing aberrations. Moreover, certain persistent higher order aberrations (HOAs) appear following the incomplete or irregular healing post-surgery that result from subtly raised features or small imperfections atop the corneal surface. These aberrations are frequently exacerbated at night when the pupil dilates to allow more light into the eye, and any post-surgical corneal roughness becomes part of the lens system. In addition, many micro-aberrations (less than 0.5-1 mm in size) unclassified by Zernike eigenvectors may contribute to poor optical quality.

The current methods of the invention as disclosed herein address to some degree lower order aberrations (LOA), higher order aberrations (HOA) and very high order aberrations, and macro- and micro-aberrations, whether arising from the tear film or from corneal surface irregularity, as well as the time varying components thereof. According to this method, the ocular surface is exposed to lubricin which noncovalently binds to the cornea and conjunctiva to create a regular, smooth optical lens with a relatively stable focal distance.

Accordingly, the invention provides a method for improving the stability of vision. According to this method, an ocular surface with a dysfunctional tear film is exposed to lubricin, and lubricin binds to the cornea to create a regular, smooth, hydrophilic surface that significantly improves tear film thinning rates and increases breakup time so that the subject can reduce blink rate and maintain a high quality retinal image during the inter-blink interval. Lubricin is believed to bind to hydrophobic basal cells and desquamated mature epithelial cells on the ocular surface to create a hydrated gel layer with a continuous, homogenous refractive index, thereby reducing scatter and other aberrations. The lubricin attachment serves as an anchor to create a diffuse network of mucins and glycoproteins that extend from the surface of the epithelium out into the aqueous layer of the tear film, the depth of which is governed largely by the equilibration of shear stress between blinks and attachment forces within the network. Accordingly, this proteoglycan matrix would fill in defects atop the ocular surface to create a homogeneous optical lens with smoothness far superior to that of the dehydrated, basal epithelium. In sections where a deeper support is located, e.g., atop an immature basal epithelial cell exposed by the sloughing of an apoptotic surface cell, sufficient lubricin and other glycoproteins can accumulate and reach out into the bulk tear film until the shear stress of a blink pulls the most radially distal molecules off from the network, allowing them to re-establish and fill in holes elsewhere. As the shear forces should gradually extend from the lid to the corneal surface, deeper layers will accumulate more lubricin due to the relative lack of shear at those depths.

In any event, it has been observed that application to the eye surface of sufficient lubricin has the effect of essentially immediately ameliorating aberrant optical effects traceable to temporary or prolonged disruption of the ocular surface and tear film. These effects include the improvement of static and dynamic visual acuity (or vision clarity over space and time), improvement in night vision, reduction in size, intensity, or elimination of halos and starbursts about relatively bright objects in a visual field, reductions in the perception of glare, and reduction or elimination of various higher order aberrations such as vertical prism, horizontal prism, astigmatism, defocus, trefoil, vertical coma, horizontal coma, quadrafoil, secondary astigmatism, and spherical aberration. These beneficial effects are achieved in appropriate patients suffering therefrom simply by depositing on the surface of the eye (typically followed by blinking to spread the solution) enough lubricin glycoprotein to repair or supplement the eye film. This is believed to require, depending on the patient, as little as about 200 ng lubricin per eye and possibly as much as 3 μg lubricin per eye. Excellent results have been achieved depositing a single drop of solution, perhaps 15 to 30 μL, of about 150 μg/mL concentration of lubricin (as measured by UV absorbance assay at A280 nm, where the protein in solution is at least 90% recombinant human lubricin). Generally, it is believed that beneficial effects are apparent with a single drop of solution comprising about 15 to 25 μg/mL lubricin, and the beneficial effects saturate with a drop comprising a lubricin concentration of perhaps 200 μg/mL.

A person readily can detect vision improvement characteristic of the invention with simple tests. One example procedure is for a volunteer to view a scene which has a halo or starburst, excessive glare, or other eye film related visual impairment. A drop of lubricin is placed in one naked eye, the patient blinks five times, then compares vision between the treated and untreated eye. A reduction or sometimes disappearance of the visual artifact is immediately noticeable by most people who suffer from these impairments.

For visual acuity, a simple test is to position any sheet of printed matter far enough away from the eye (with or without eyeglasses, and indoors in ordinary daylight or in artificial light), such that the printed letters are on the edge of clarity or readability for that person: in other words, at a position where, if the sheet is moved a bit closer, the print is readable by the test patient, and if moved a bit further away, the print is indistinct and unreadable or barely readable. The patient then applies an eye drop containing lubricin to the naked eye, blinks five times, then again gazes at the sheet which is maintained at this "edge of clarity" position. Essentially all volunteers who take this test immediately report that the print is easier to read and that their vision is more acute after lubricin application. The effect often can be made more noticeable by comparing vision through the lubricin-treated eye to the untreated eye. Similarly, people suffering from a halo effect, e.g., as a side effect of eye surgery such as LASIK, cataract surgery, or the like, report a reduction or disappearance of halos after self-administration of one or more lubricin drops in one or both eyes. Indeed, volunteers report an improvement in vision comparable to moving from a standard definition to a high definition television following topical instillation of lubricin.

Thus, patients with tired eyes, irritated eyes, e.g., have worn contact lenses for a prolonged period and suffer from a destabilized tear film and shortened break-up time, suffering from poor night vision, starbursts or halos, or higher order anomalies, in accordance with the invention, can carry a suitable applicator of lubricin eye drops and apply a drop in either eye as necessary to relieve symptoms.

Lubricin

Lubricin is now well known. Its full length amino acid sequence (secretion signal in bold) is set forth in FIG. 2 (NCBI Accession Numbers AK131434 and U70136). The human gene encoding it is set forth in FIG. 3. It is a polypeptide with surface lubricating properties expressed from the megakaryocyte stimulating factor (MSF) gene, also known as PRG4. Its natural form in all mammals investigated contains multiple repeats of an amino acid sequence which is at least 50% identical to the sequence KEPAPTT (SEQ ID NO: 3). Natural lubricins typically comprise multiple redundant forms of this repeat, but typically always include proline and threonine residues, with at least one threonine being glycosylated in some, most, or all repeats. The threonine anchored O-linked sugar side chains are critical for lubricin's boundary lubricating function. The side chain moiety typically is a β-(1-3)-Gal-GalNac moiety. Optionally, the β-(1-3)-Gal-GalNac is capped with sialic or N-acetylneuraminic acid or NeuAc. The polypeptide also typically comprises N-linked oligosaccharides. Lubricin is polydisperse in that individual lubricin molecules differ in their degree and pattern of glycosylation.

The amino acid sequence of the protein backbone of lubricin may differ depending on alternative splicing of exons of the human MSF gene. This robustness against heterogeneity was exemplified when researchers created a recombinant form of lubricin missing 474 amino acids from the central mucin domain, yet still achieved reasonable, although muted, lubrication (Flannery et al., Arthritis Rheum 2009; 60(3):840-7). PRG4 has been shown to exist not only as a monomer but also as a dimer and multimer disulfide-bonded through the conserved cysteine-rich domains at both N- and C-termini. Lubris, LLC has developed a full-length recombinant form of human lubricin. The molecule is expressed using the Selexis Chinese hamster ovary cell line (CHO-M), with a final apparent molecular weight of 450-600 kDa, with polydisperse multimers frequently measuring at 2,000 kDa or more, all as estimated by comparison to molecular weight standards on SDS trisacetate 3-8% polyacrylamide gels. Of the total glycosylations, about half of the molecules contain two sugar units (GalNAc-Gal), and half three sugar units (GalNAc-Gal-Sialic acid). This method of recombinant human PRG4 production is provided in International Patent Application Publication No. WO 2015/061488, the disclosure of which is incorporated herein by reference.

All useful molecules comprise the sequence encoded by exon 6, or homologs or truncated versions thereof, for example, versions with fewer repeats within this central mucin-like KEPAPTT-repeat domain (SEQ ID NO:3), together with O-linked glycosylation. All useful molecules also comprise at least the biological active portions of the sequences encoded by exons 1-5 and 7-12, i.e., sequences responsible for imparting to the molecule its affinity for extracellular matrix and endothelial surfaces. In certain embodiments, lubricin protein has an average molar mass of between 50 kDa and 500 kDa, preferably between 224 to 467 kDa, comprising one or more biological active portions of the PRG4 protein, or functional fragments, such as a lubricating fragment, or a homolog thereof. In a more preferred embodiment, a PRG4 protein comprises monomers of average molar mass of between 220 kDa to about 280 kDa.

Methods for isolation of lubricin from natural sources, for its purification, and for its recombinant expression are well known in the art. As disclosed in International Patent Application Publication No. WO 2015/061488, recombinant production methods start with cloning and isolating mRNA and cDNA encoding PRG4 proteins or isoforms using standard molecular biology techniques, such as PCR or RT-PCR. The isolated cDNA encoding the PRG4 protein or isoform is then cloned into an expression vector, preferably CHO-M, and further transformed and expressed in a host cell for producing recombinant PRG4 protein. Purification involves empirical experimentation to develop the most efficient protocol which effectively removes host cell proteins, inhibits aggregation, and remove virus and other contaminants.

Any one or more of various native and recombinant PRG4 proteins and isoforms may be utilized in methods described herein. For instance, U.S. Pat. Nos. 6,433,142; 6,743,774; 6,960,562; 7,030,223, and 7,361,738 disclose how to make various forms of human PRG4 expression product, each of which is incorporated herein by reference. Preferred for use in the practice of the invention is full length, robustly glycosylated, recombinant lubricin, expressed from CHO-M cells, as disclosed in the above referenced PCT application. This protein comprises 1404 amino acids including a central exon comprising repeats of the sequence KEPAPTT (SEQ ID NO:3) variously glycosylated with O-linked β (1-3) Gal-GalNAc oligosaccharides, and including N and C-terminal sequences with homology to vitronectin. Its sequence is disclosed in FIG. 2. The molecule is polydisperse with the glycosylation pattern of individual molecules varying, and can comprise monomeric, dimeric, and multimeric species.

Lubricin Eye Drop Formulation

The eye drops suitable for topical application to an ocular surface comprise a therapeutically effective concentration of a PRG4 protein disposed in an ophthalmically acceptable balanced salt solution, e.g., phosphate buffered saline. Ophthalmically acceptable compositions are considered suitable for topical application to the ocular surface if, upon application, they lack unacceptable eye toxicity, burning, itchiness, viscosity, etc. The concentration of lubricin may vary widely, from a few micrograms per milliliter to as many as 200 or 300 micrograms per milliliter. More dilute solutions may permit the patient to titrate the therapeutic dose to suit his or her vision anomaly by adding multiple drops.

In certain embodiments, the eye drops used in the present invention also may comprise one or more optional ingredients such as an ophthalmically acceptable demulcent, excipient, astringent, vasoconstrictor, or emollient. The aqueous lubricin glycoprotein solutions used in the method of the present invention optionally further may comprises a therapeutically effective concentration of one or more additional therapeutic agents, including for example sodium hyaluronate, hyaluronic acid, and/or phospholipid. Exemplary phospholipids include L-α-dipalmitoylphosphatidylcholine, phosphatidylcholine, phosphatidylethanolamine and sphingomyelin. The lubricin typically is dissolved in an ophthalmically acceptable balanced salt solution comprising at least three electrolytes, including, for example, sodium chloride (NaCl) 0.64%, potassium chloride (KCl) 0.075%, calcium chloride dihydrate ($CaCl_2.2H_2O$) 0.048%, magnesium chloride hexahydrate ($MgCl_2.6H_2O$) 0.03%, sodium acetate trihydrate ($C_2H_3NaO_2.3H2O$) 0.39%, sodium citrate dihydrate ($C_6H_5Na_3O_7.2H_2O$) 0.17%, and sodium hydroxide and/or hydrochloric acid (to adjust pH to approximately 7.5) with an osmolarity of approximately 300 mOsms/L. In other embodiments, the aqueous vehicle may comprises 128 mM sodium, 24 mM potassium, approximately 113 mM chloride, approximately 0.4 mM calcium, approximately 0.3 mM magnesium, approximately 5 mM $HCO3^-$, approximately 1 mM citrate, approximately 14 mM phosphate, approximately 15 mM acetate, and sodium hydroxide and/or hydrochloric acid sufficient to adjust pH to approximately 7.5, and with an osmolarity of approximately 200-300 mOsm/L.

Other embodiments are within the following claims.

What is claimed is:

1. A method of treating a visual aberration due to corneal surface irregularity in an eye of a human patient comprising depositing onto the surface of the eye or of each eye of said patient an amount of 10-100 microliters of an ophthalmically acceptable solution comprising lubricin at a concentration within a range of from 10 μg/mL to 300 μg/mL to form a hydrated gel layer of lubricin across the corneal surface of the eye or of each eye, thereby to alleviate said visual aberration, wherein the visual aberration is selected from the group consisting of diminished night vision, visual halo, visual starburst, loss of static visual acuity, visual glare, and higher order aberrations.

2. The method of claim 1, wherein the patient has had prior eye surgery selected from the group consisting of cataract surgery, laser in-situ keratomileusis (LASIK), photorefractive keratectomy (PRK), laser epithelial keratomileusis (LASEK), refractive lens exchange (RLE) and presbyopic lens exchange (PRELEX).

3. The method of claim 1, wherein 15 to 30 microliters of said solution are deposited on the surface of the eye or the surface of each of the eyes of said patient.

4. The method of claim 1, wherein the solution comprises the lubricin at a concentration within a range of from 50 μg/mL to 200 μg/mL.

5. The method of claim 1, wherein the solution comprises an ophthalmically acceptable surface active phospholipid selected from the group consisting of L-α-dipalmitoylphosphatidylcholine, phosphatidylcholine, phosphatidylethanolamine and sphingomyelin.

6. The method of claim 1, wherein the solution comprises a phosphate buffered saline solution comprising at least sodium phosphate and sodium chloride.

7. The method of claim 1, wherein the solution comprises an ophthalmically acceptable balanced salt solution comprising one or more electrolytes selected from the group consisting of potassium chloride, sodium bicarbonate, potassium bicarbonate, calcium chloride, magnesium chloride, a sodium citrate, hydrochloric acid, and sodium hydroxide.

8. The method of claim 1, wherein the solution comprises hyaluronate salt or hyaluronic acid.

9. The method of claim 1, wherein the patient has not been diagnosed with dry eye disease.

10. The method of claim 1, wherein the lubricin comprises the amino acid sequence of SEQ ID NO:1 less the signal sequence.

11. The method of claim 1, wherein the depositing lubricin onto the surface of the eye results in essentially immediate amelioration of the visual aberration.

12. The method of claim 1, wherein the corneal surface irregularity is caused by damage to the corneal epithelium.

13. The method of claim 2, wherein the cataract surgery, laser in-situ keratomileusis (LASIK), photorefractive keratectomy (PRK), laser epithelial keratomileusis (LASEK), refractive lens exchange (RLE) or presbyopic lens exchange (PRELEX), causes damage to the corneal epithelium, resulting in the corneal surface irregularity.

14. The method of claim 13, wherein the lubricin comprises the amino acid sequence of SEQ ID NO:1 less the signal sequence.

15. The method of claim 13, wherein the patient has not been diagnosed with dry eye disease.

16. The method of claim 13, wherein the depositing lubricin onto the surface of the eye results in essentially immediate amelioration of the visual aberration.

17. The method of claim 13, wherein the higher order aberration is selected from the group consisting of vertical prism, horizontal prism, astigmatism, defocus, trefoil, vertical coma, horizontal coma, quatrefoil, secondary astigmatism, spherical aberration, an aberration described by higher order Zernike polynomials, micro-aberrations, or macro-aberrations.

18. The method of claim 1, wherein the higher order aberration is selected from the group consisting of vertical prism, horizontal prism, astigmatism, defocus, trefoil, vertical coma, horizontal coma, quatrefoil, secondary astigmatism, spherical aberration, an aberration described by higher order Zernike polynomials, micro-aberrations, and macro-aberrations.

\* \* \* \* \*

SEQUENCE LISTING

```
<160> NUMBER OF SEQ ID NOS: 3

<210> SEQ ID NO 1
<211> LENGTH: 1404
<212> TYPE: PRT
<213> ORGANISM: Homo sapiens

<400> SEQUENCE: 1

Met Ala Trp Lys Thr Leu Pro Ile Tyr Leu Leu Leu Leu Ser Val
1               5                   10                  15

Phe Val Ile Gln Gln Val Ser Ser Gln Asp Leu Ser Ser Cys Ala Gly
            20                  25                  30

Arg Cys Gly Glu Gly Tyr Ser Arg Asp Ala Thr Cys Asn Cys Asp Tyr
        35                  40                  45

Asn Cys Gln His Tyr Met Glu Cys Cys Pro Asp Phe Lys Arg Val Cys
    50                  55                  60

Thr Ala Glu Leu Ser Cys Lys Gly Arg Cys Phe Glu Ser Phe Glu Arg
65                  70                  75                  80

Gly Arg Glu Cys Asp Cys Asp Ala Gln Cys Lys Lys Tyr Asp Lys Cys
                85                  90                  95

Cys Pro Asp Tyr Glu Ser Phe Cys Ala Glu Val His Asn Pro Thr Ser
            100                 105                 110
```

```
-continued

Pro Pro Ser Ser Lys Lys Ala Pro Pro Ser Gly Ala Ser Gln Thr
        115                 120                 125

Ile Lys Ser Thr Thr Lys Arg Ser Pro Lys Pro Pro Asn Lys Lys
    130                 135                 140

Thr Lys Lys Val Ile Glu Ser Glu Glu Ile Thr Glu Glu His Ser Val
145                 150                 155                 160

Ser Glu Asn Gln Glu Ser Ser Ser Ser Ser Ser Ser Ser Ser Ser
                165                 170                 175

Ser Thr Ile Arg Lys Ile Lys Ser Ser Lys Asn Ser Ala Ala Asn Arg
            180                 185                 190

Glu Leu Gln Lys Lys Leu Lys Val Lys Asp Asn Lys Lys Asn Arg Thr
            195                 200                 205

Lys Lys Lys Pro Thr Pro Lys Pro Pro Val Val Asp Glu Ala Gly Ser
        210                 215                 220

Gly Leu Asp Asn Gly Asp Phe Lys Val Thr Thr Pro Asp Thr Ser Thr
225                 230                 235                 240

Thr Gln His Asn Lys Val Ser Thr Ser Pro Lys Ile Thr Thr Ala Lys
                245                 250                 255

Pro Ile Asn Pro Arg Pro Ser Leu Pro Pro Asn Ser Asp Thr Ser Lys
            260                 265                 270

Glu Thr Ser Leu Thr Val Asn Lys Glu Thr Thr Val Glu Thr Lys Glu
        275                 280                 285

Thr Thr Thr Thr Asn Lys Gln Thr Ser Thr Asp Gly Lys Glu Lys Thr
            290                 295                 300

Thr Ser Ala Lys Glu Thr Gln Ser Ile Glu Lys Thr Ser Ala Lys Asp
305                 310                 315                 320

Leu Ala Pro Thr Ser Lys Val Leu Ala Lys Pro Thr Pro Lys Ala Glu
                325                 330                 335

Thr Thr Thr Lys Gly Pro Ala Leu Thr Thr Pro Lys Glu Pro Thr Pro
            340                 345                 350

Thr Thr Pro Lys Glu Pro Ala Ser Thr Thr Pro Lys Glu Pro Thr Pro
        355                 360                 365

Thr Thr Ile Lys Ser Ala Pro Thr Thr Pro Lys Glu Pro Ala Pro Thr
    370                 375                 380

Thr Thr Lys Ser Ala Pro Thr Thr Pro Lys Glu Pro Ala Pro Thr Thr
385                 390                 395                 400

Thr Lys Glu Pro Ala Pro Thr Thr Pro Lys Glu Pro Ala Pro Thr Thr
                405                 410                 415

Thr Lys Glu Pro Ala Pro Thr Thr Thr Lys Ser Ala Pro Thr Thr Pro
            420                 425                 430

Lys Glu Pro Ala Pro Thr Thr Pro Lys Lys Pro Ala Pro Thr Thr Pro
        435                 440                 445

Lys Glu Pro Ala Pro Thr Thr Pro Lys Glu Pro Thr Pro Thr Thr Pro
    450                 455                 460

Lys Glu Pro Ala Pro Thr Thr Lys Glu Pro Ala Pro Thr Thr Pro Lys
465                 470                 475                 480

Glu Pro Ala Pro Thr Ala Pro Lys Lys Pro Ala Pro Thr Thr Pro Lys
                485                 490                 495

Glu Pro Ala Pro Thr Thr Pro Lys Glu Pro Ala Pro Thr Thr Thr Lys
            500                 505                 510

Glu Pro Ser Pro Thr Thr Pro Lys Glu Pro Ala Pro Thr Thr Thr Lys
        515                 520                 525

Ser Ala Pro Thr Thr Thr Lys Glu Pro Ala Pro Thr Thr Thr Lys Ser
```

```
                530             535             540
Ala Pro Thr Thr Pro Lys Glu Pro Ser Pro Thr Thr Thr Lys Glu Pro
545                 550             555                 560

Ala Pro Thr Thr Pro Lys Glu Pro Ala Pro Thr Thr Pro Lys Lys Pro
                565             570                 575

Ala Pro Thr Thr Pro Lys Glu Pro Ala Pro Thr Thr Pro Lys Glu Pro
                580             585                 590

Ala Pro Thr Thr Thr Lys Lys Pro Ala Pro Thr Thr Pro Lys Glu Pro
                595             600                 605

Ala Pro Thr Thr Pro Lys Glu Thr Ala Pro Thr Thr Pro Lys Lys Leu
                610             615                 620

Thr Pro Thr Thr Pro Glu Lys Leu Ala Pro Thr Thr Pro Glu Lys Pro
625                 630             635                 640

Ala Pro Thr Thr Pro Glu Glu Leu Ala Pro Thr Thr Pro Glu Glu Pro
                645             650                 655

Thr Pro Thr Thr Pro Glu Glu Pro Ala Pro Thr Thr Pro Lys Ala Ala
                660             665                 670

Ala Pro Asn Thr Pro Lys Glu Pro Ala Pro Thr Thr Pro Lys Glu Pro
                675             680                 685

Ala Pro Thr Thr Pro Lys Glu Pro Ala Pro Thr Thr Pro Lys Glu Thr
                690             695                 700

Ala Pro Thr Thr Pro Lys Gly Thr Ala Pro Thr Thr Leu Lys Glu Pro
705                 710             715                 720

Ala Pro Thr Thr Pro Lys Lys Pro Ala Pro Lys Glu Leu Ala Pro Thr
                725             730                 735

Thr Thr Lys Glu Pro Thr Ser Thr Thr Cys Asp Lys Pro Ala Pro Thr
                740             745                 750

Thr Pro Lys Gly Thr Ala Pro Thr Thr Pro Lys Glu Pro Ala Pro Thr
                755             760                 765

Thr Pro Lys Glu Pro Ala Pro Thr Thr Pro Lys Gly Thr Ala Pro Thr
                770             775                 780

Thr Leu Lys Glu Pro Ala Pro Thr Thr Pro Lys Lys Pro Ala Pro Lys
785                 790             795                 800

Glu Leu Ala Pro Thr Thr Thr Lys Gly Pro Thr Ser Thr Thr Ser Asp
                805             810                 815

Lys Pro Ala Pro Thr Thr Pro Lys Glu Thr Ala Pro Thr Thr Pro Lys
                820             825                 830

Glu Pro Ala Pro Thr Thr Pro Lys Lys Pro Ala Pro Thr Thr Pro Glu
                835             840                 845

Thr Pro Pro Pro Thr Thr Ser Glu Val Ser Thr Pro Thr Thr Thr Lys
850                 855             860

Glu Pro Thr Thr Ile His Lys Ser Pro Asp Glu Ser Thr Pro Glu Leu
865                 870             875                 880

Ser Ala Glu Pro Thr Pro Lys Ala Leu Glu Asn Ser Pro Lys Glu Pro
                885             890                 895

Gly Val Pro Thr Thr Lys Thr Pro Ala Ala Thr Lys Pro Glu Met Thr
                900             905                 910

Thr Thr Ala Lys Asp Lys Thr Glu Arg Asp Leu Arg Thr Thr Pro
                915             920                 925

Glu Thr Thr Thr Ala Ala Pro Lys Met Thr Lys Glu Thr Ala Thr Thr
                930             935                 940

Thr Glu Lys Thr Thr Glu Ser Lys Ile Thr Ala Thr Thr Thr Gln Val
945                 950             955                 960
```

```
Thr Ser Thr Thr Thr Gln Asp Thr Thr Pro Phe Lys Ile Thr Thr Leu
            965                 970                 975
Lys Thr Thr Thr Leu Ala Pro Lys Val Thr Thr Thr Lys Lys Thr Ile
            980                 985                 990
Thr Thr Thr Glu Ile Met Asn Lys Pro Glu Glu Thr Ala Lys Pro Lys
            995                 1000                1005
Asp Arg Ala Thr Asn Ser Lys Ala Thr Thr Pro Lys Pro Gln Lys
        1010            1015                1020
Pro Thr Lys Ala Pro Lys Lys Pro Thr Ser Thr Lys Lys Pro Lys
        1025            1030                1035
Thr Met Pro Arg Val Arg Lys Pro Lys Thr Thr Pro Thr Pro Arg
        1040            1045                1050
Lys Met Thr Ser Thr Met Pro Glu Leu Asn Pro Thr Ser Arg Ile
        1055            1060                1065
Ala Glu Ala Met Leu Gln Thr Thr Thr Arg Pro Asn Gln Thr Pro
        1070            1075                1080
Asn Ser Lys Leu Val Glu Val Asn Pro Lys Ser Glu Asp Ala Gly
        1085            1090                1095
Gly Ala Glu Gly Glu Thr Pro His Met Leu Leu Arg Pro His Val
        1100            1105                1110
Phe Met Pro Glu Val Thr Pro Asp Met Asp Tyr Leu Pro Arg Val
        1115            1120                1125
Pro Asn Gln Gly Ile Ile Ile Asn Pro Met Leu Ser Asp Glu Thr
        1130            1135                1140
Asn Ile Cys Asn Gly Lys Pro Val Asp Gly Leu Thr Thr Leu Arg
        1145            1150                1155
Asn Gly Thr Leu Val Ala Phe Arg Gly His Tyr Phe Trp Met Leu
        1160            1165                1170
Ser Pro Phe Ser Pro Pro Ser Pro Ala Arg Arg Ile Thr Glu Val
        1175            1180                1185
Trp Gly Ile Pro Ser Pro Ile Asp Thr Val Phe Thr Arg Cys Asn
        1190            1195                1200
Cys Glu Gly Lys Thr Phe Phe Phe Lys Asp Ser Gln Tyr Trp Arg
        1205            1210                1215
Phe Thr Asn Asp Ile Lys Asp Ala Gly Tyr Pro Lys Pro Ile Phe
        1220            1225                1230
Lys Gly Phe Gly Gly Leu Thr Gly Gln Ile Val Ala Ala Leu Ser
        1235            1240                1245
Thr Ala Lys Tyr Lys Asn Trp Pro Glu Ser Val Tyr Phe Phe Lys
        1250            1255                1260
Arg Gly Gly Ser Ile Gln Gln Tyr Ile Tyr Lys Gln Glu Pro Val
        1265            1270                1275
Gln Lys Cys Pro Gly Arg Arg Pro Ala Leu Asn Tyr Pro Val Tyr
        1280            1285                1290
Gly Glu Thr Thr Gln Val Arg Arg Arg Phe Glu Arg Ala Ile
        1295            1300                1305
Gly Pro Ser Gln Thr His Thr Ile Arg Ile Gln Tyr Ser Pro Ala
        1310            1315                1320
Arg Leu Ala Tyr Gln Asp Lys Gly Val Leu His Asn Glu Val Lys
        1325            1330                1335
Val Ser Ile Leu Trp Arg Gly Leu Pro Asn Val Val Thr Ser Ala
        1340            1345                1350
```

```
Ile Ser Leu Pro Asn Ile Arg Lys Pro Asp Gly Tyr Asp Tyr Tyr
    1355            1360                1365

Ala Phe Ser Lys Asp Gln Tyr Tyr Asn Ile Asp Val Pro Ser Arg
1370                1375                1380

Thr Ala Arg Ala Ile Thr Thr Arg Ser Gly Gln Thr Leu Ser Lys
1385                1390                1395

Val Trp Tyr Asn Cys Pro
        1400

<210> SEQ ID NO 2
<211> LENGTH: 5041
<212> TYPE: DNA
<213> ORGANISM: Homo sapiens

<400> SEQUENCE: 2
gcggccgcga ctattcggta cctgaaaaca acgatggcat ggaaaacact tcccatttac      60
ctgttgttgc tgctgtctgt tttcgtgatt cagcaagttt catctcaaga tttatcaagc     120
tgtgcaggga gatgtgggga agggtattct agagatgcca cctgcaactg tgattataac     180
tgtcaacact acatggagtg ctgccctgat ttcaagagag tctgcactgc ggagcttttcc    240 tgtaaaggcc gctgctttga gtccttcgag agagggaggg agtgtgactg cgacgcccaa     300
tgtaagaagt atgacaagtg ctgtcccgat tatgagagtt tctgtgcaga agtgcataat     360
cccacatcac caccatcttc aaagaaagca cctccacctt caggagcatc tcaaaccatc     420
aaatcaacaa ccaaacgttc acccaaacca caaacaaga agaagactaa gaaagttata     480
gaatcagagg aaataacaga gaacattct gtttctgaaa atcaagagtc ctcctcctcc      540
tcctcctctt cctcttcttc ttcaacaatt tggaaaatca agtcttccaa aaattcagct     600
gctaatagag aattacagaa gaaactcaaa gtaaagata caagaagaa cagaactaaa      660 aagaaaccta cccccaaacc accagttgta gatgaagctg aagtggatt ggacaatggt     720 gacttcaagg tcacaactcc tgacacgtct accacccaac acaataaagt cagcacatct    780
cccaagatca acacagcaaa accaataaat cccagaccca gtcttccacc taattctgat    840
acatctaaag agacgtcttt gacagtgaat aaagagacaa cagttgaaac taagaaaact     900
actacaacaa ataaacagac ttcaactgat ggaaaagaga agactacttc cgctaaagag    960
acacaaagta tagagaaaac atctgctaaa gatttagcac ccacatctaa agtgctggct   1020
aaacctacac ccaaagctga actacaacc aaaggccctg ctctcaccac tcccaaggag   1080
cccacgccca ccactcccaa ggagcctgca tctaccacac ccaaagagcc acacctacc   1140 accatcaagt ctgcacccac cacccccaag gagcctgcac caccaccac aagtctgca    1200 cccaccactc ccaaggagcc tgcacccacc accaccaagg agcctgcacc caccactccc   1260
aaggagcctg cacccaccac caccaaggag cctgcaccca ccaccaa gtctgcaccc     1320 accactccca aggagcctgc acccaccacc ccaagaagc tgccccaac tacccccaag   1380 gagcctgcac ccaccactcc caaggagcct acacccacca ctcccaagga gcctgcaccc   1440
accaccaagg agcctgcacc accactcccc aaagagcctg cacccactgc ccccaagaag   1500
cctgccccaa ctaccccaa ggagcctgca cccaccactc caaggagcc tgcacccacc     1560 accaccaagg agccttcacc caccactccc aaggagcctg cacccaccac caccaagtct   1620
gcacccacca ctaccaagga gcctgcaccc accactacca gtctgcacc caccactccc   1680 aaggagcctt cacccaccac caccaaggag cctgcaccca ccactccaa ggagcctgca    1740 cccaccaccc caagaagcc tgccccaact accccaagg agcctgcacc caccactccc    1800
```

```
aaggaacctg cacccaccac caccaagaag cctgcaccca ccgctcccaa agagcctgcc    1860
ccaactaccc ccaaggagac tgcacccacc acccccaaga agctcacgcc cacccccccc    1920
gagaagctcg cacccaccac ccctgagaag cccgcaccca ccaccccctga ggagctcgca   1980 cccaccaccc ctgaggagcc cacacccacc acccctgagg agcctgctcc caccactccc    2040
aaggcagcgg ctcccaacac ccctaaggag cctgctccaa ctaccccctaa ggagcctgct   2100 ccaactaccc ctaaggagcc tgctccaact accccctaagg agactgctcc aactaccccct  2160 aaagggactg ctccaactac cctcaaggaa cctgcaccca ctactcccaa gaagcctgcc    2220
cccaaggagc ttgcacccac caccaccaag agcccacat ccaccacctc tgacaagccc     2280
gctccaacta cccctaaggg gactgctcca actacccccta aggagcctgc tccaactacc   2340
cctaaggagc ctgctccaac taccccctaag gggactgctc caactaccct caaggaacct   2400
gcacccacta ctcccaagaa gcctgccccc aaggagcttg cacccaccac caccaagggg   2460
cccacatcca ccacctctga caagcctgct ccaactacac ctaaggagac tgctccaact   2520 accccccaagg agcctgcacc cactaccccc aagaagcctg ctccaactac tcctgagaca   2580
cctcctccaa ccacttcaga ggtctctact ccaactacca ccaaggagcc taccactatc    2640
cacaaaagcc ctgatgaatc aactcctgag ctttctgcag aacccacacc aaaagctctt    2700
gaaaacagtc ccaaggaacc tggtgtacct acaactaaga ctcctgcagc gactaaacct    2760
gaaatgacta caacagctaa agacaagaca acagaaagag acttacgtac tacacctgaa    2820
actacaactg ctgcacctaa gatgacaaaa gagacagcaa ctacaacaga aaaaactacc    2880
gaatccaaaa taacagctac aaccacacaa gtaacatcta ccacaactca agataccaca    2940
ccattcaaaa ttactactct taaaacaact actcttgcac ccaaagtaac tacaacaaaa    3000
aagacaatta ctaccactga gattatgaac aaacctgaag aaacagctaa accaaaagac    3060
agagctacta attctaaagc gacaactcct aaacctcaaa agccaaccaa agcacccaaa    3120
aaacccactt ctaccaaaaa gccaaaaaca atgcctagag tgagaaaacc aaagacgaca    3180
ccaactcccc gcaagatgac atcaacaatg ccagaattga ccctacctc aagaatagca    3240 gaagccatgc tccaaaccac caccagacct aaccaaactc caaactccaa actagttgaa    3300
gtaaatccaa agagtgaaga tgcaggtggt gctgaaggag aaacacctca tatgcttctc    3360
aggccccatg tgttcatgcc tgaagttact cccgacatgg attacttacc gagagtaccc    3420
aatcaaggca ttatcatcaa tcccatgctt tccgatgaga ccaatatatg caatggtaag    3480
ccagtagatg gactgactac tttgcgcaat gggacattag ttgcattccg aggtcattat    3540
ttctggatgc taagtccatt cagtccacca tctccagctc gcagaattac tgaagtttgg    3600
ggtattcctt cccccattga tactgttttt actaggtgca actgtgaagg aaaaactttc    3660
ttctttaagg attctcagta ctggcgtttt accaatgata taaaagatgc agggtacccc    3720
aaaccaattt tcaaaggatt tggaggacta actggacaaa tagtggcagc gctttcaaca    3780
gctaaatata agaactggcc tgaatctgtg tattttttca agagaggtgg cagcattcag    3840
cagtatattt ataaacagga acctgtacag aagtgccctg aagaaggcc tgctctaaat    3900 tatccagtgt atggagaaat gacacaggtt aggagacgtc gctttgaacg tgctatagga    3960
ccttctcaaa cacacaccat cagaattcaa tattcacctg ccagactggc ttatcaagac    4020
aaaggtgtcc ttcataatga agttaaagtg agtatactgt ggagaggact tccaaatgtg    4080
gttacctcag ctatatcact gcccaacatc agaaaacctg acggctatga ttactatgcc    4140
```

```
ttttctaaag atcaatacta taacattgat gtgcctagta gaacagcaag agcaattact    4200
actcgttctg ggcagacctt atccaaagtc tggtacaact gtccttagac tgatgagcaa    4260
aggaggagtc aactaatgaa gaaatgaata ataaattttg acactgaaaa acattttatt    4320
aataaagaat attgacatga gtataccagt ttatatataa aaatgttttt aaacttgaca    4380
atcattacac taaaacagat ttgataatct tattcacagt tgttattgtt tacagaccat    4440
ttaattaata tttcctctgt ttattcctcc tctccctccc attgcatggc tcacacctgt    4500
aaaagaaaaa agaatcaaat tgaatatatc ttttaagaat tcaaaactag tgtattcact    4560
taccctagtt cattataaaa aatatctagg cattgtggat ataaaactgt tgggtattct    4620
acaacttcaa tggaaattat tacaagcaga ttaatccctc tttttgtgac acaagtacaa    4680
tctaaaagtt atattggaaa acatggaaat attaaaattt tacactttta ctagctaaaa    4740
cataatcaca aagctttatc gtgttgtata aaaaaattaa caatataatg gcaataggta    4800
gagatacaac aaatgaatat aacactataa cacttcatat tttccaaatc ttaatttgga    4860
tttaaggaag aaatcaataa atataaaata taagcacata tttattatat atctaaggta    4920
tacaaatctg tctacatgaa gtttacagat tggtaaatat cacctgctca acatgtaatt    4980
atttaataaa actttggaac attaaaaaaa taaattggag gcttaaaaaa aaaaaaaaaa    5040
a                                                                   5041

<210> SEQ ID NO 3
<211> LENGTH: 7
<212> TYPE: PRT
<213> ORGANISM: Homo sapiens

<400> SEQUENCE: 3

Lys Glu Pro Ala Pro Thr Thr
1               5
```

UNITED STATES PATENT AND TRADEMARK OFFICE
CERTIFICATE OF CORRECTION

PATENT NO. : 11,666,529 B2
APPLICATION NO. : 15/574712
DATED : June 6, 2023
INVENTOR(S) : Sullivan et al.

Page 1 of 1

It is certified that error appears in the above-identified patent and that said Letters Patent is hereby corrected as shown below:

In the Claims

In Claim 17, at Column 23, Lines 14-15 replace "or macro-aberrations" with --and macro-aberrations--.

Signed and Sealed this
Twenty-fifth Day of July, 2023

Katherine Kelly Vidal
*Director of the United States Patent and Trademark Office*